US00PP12463P2

(12) United States Plant Patent
Noodelijk

(10) Patent No.: US PP12,463 P2
(45) Date of Patent: Mar. 12, 2002

(54) CHRYSANTHEMUM PLANT NAMED 'VALENTIN'

(75) Inventor: Robert Noodelijk, Woubrugge (NL)

(73) Assignee: Chrysanthemum Breeders Association, N.V. (NL)

( * ) Notice: Subject to any disclaimer, the term of this patent is extended or adjusted under 35 U.S.C. 154(b) by 0 days.

(21) Appl. No.: 09/561,935

(22) Filed: May 1, 2000

(51) Int. Cl.[7] ..... A01H 5/00
(52) U.S. Cl. ..... Plt./297
(58) Field of Search ..... Plt./297

*Primary Examiner*—Bruce R. Campell
*Assistant Examiner*—Annette H. Para
(74) *Attorney, Agent, or Firm*—Parkhurst & Wendel, L.L.P.

(57) ABSTRACT

A Chrysanthemum plant named 'Valentin' characterized by its SMALL sized blooms with PALE PINK ray-florets and YELLOW-GREEN disc florets.

2 Drawing Sheets

BACKGROUND OF THE INVENTION

'VALENTIN' is a product of a breeding-program which had the objective of creating new chrysanthemum cultivars with a small type flower, a 7 week response and a compact plant height. The new plant of the present invention comprises a new and distinct cultivar of Chrysanthemum plant. 'VALENTIN' is a seedling from a cross in a breeding program maintained under the control of inventor. The female parent is #92.0424-unpatented-, an unamed seedling not available to inventor for description. The male parent is unknown, being a mixed pollation of a group of male parents. The new and distinct cultivar was discovered and selected as a flowering plant within the progeny of the stated cross by Rob Noodelijk in a controlled environment (greenhouse) in Rijsenhout Holland in May 1998. The first act of asexual reproduction of 'VALENTIN' was accomplished when vegetative cuttings were taken from the initial selection in August 1998 in a controlled environment in Rijsenhout Holland.

SUMMARY OF THE INVENTION

The present invention is a new and distinct variety of chrysanthemum bearing small sized blooms with pale pink ray-florets and yellow-green disc florets.

BRIEF DESCRIPTION OF THE DRAWINGS

The present invention of a new and distinct variety of chrysanthemem is shown in the accompanying drawings, the color being as nearly true as possible with color photographs of this type.

DESCRIPTION OF THE INVENTION

Figure 1:
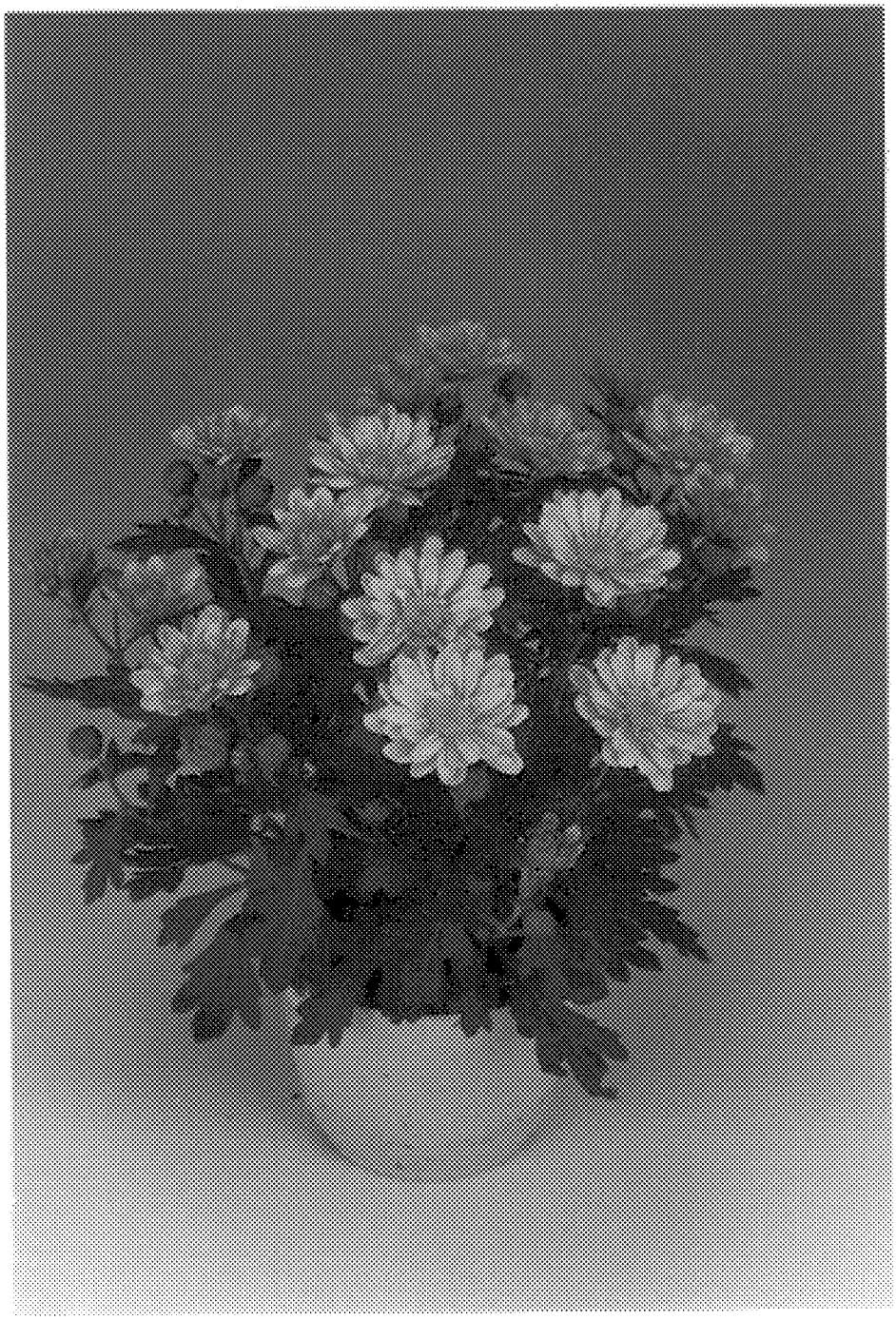
FIG. 1 shows a plant of the cultivar in full bloom.
Figure 2:
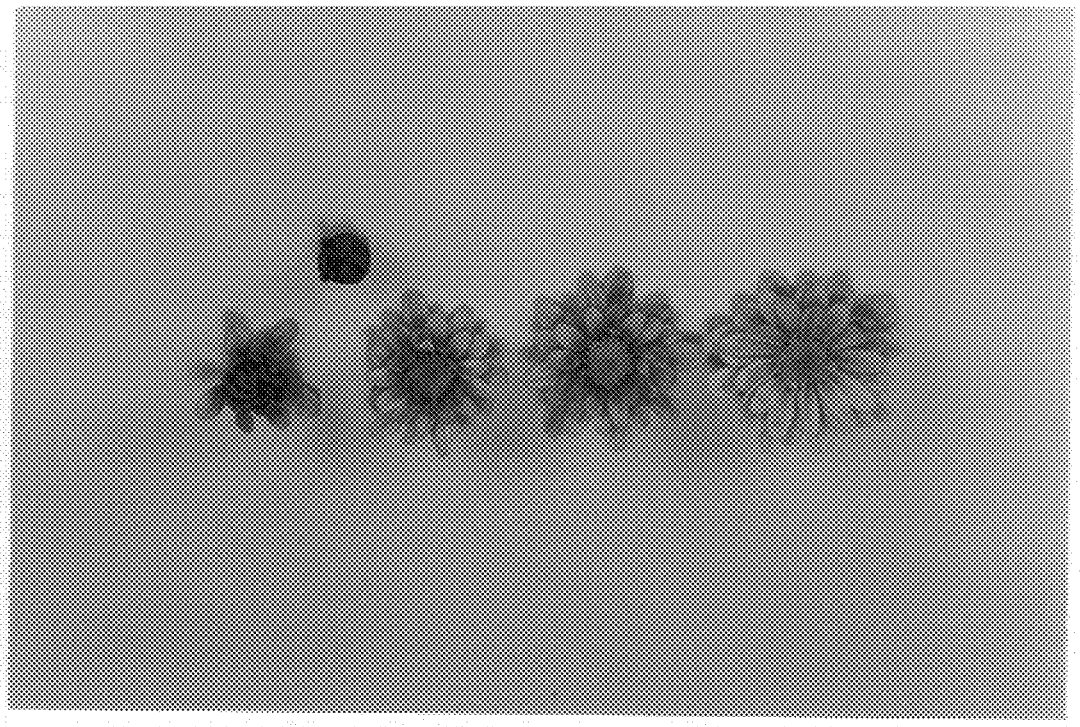
FIG. 2 shows the various stages of bloom of the new cultivar.
Figure 3:
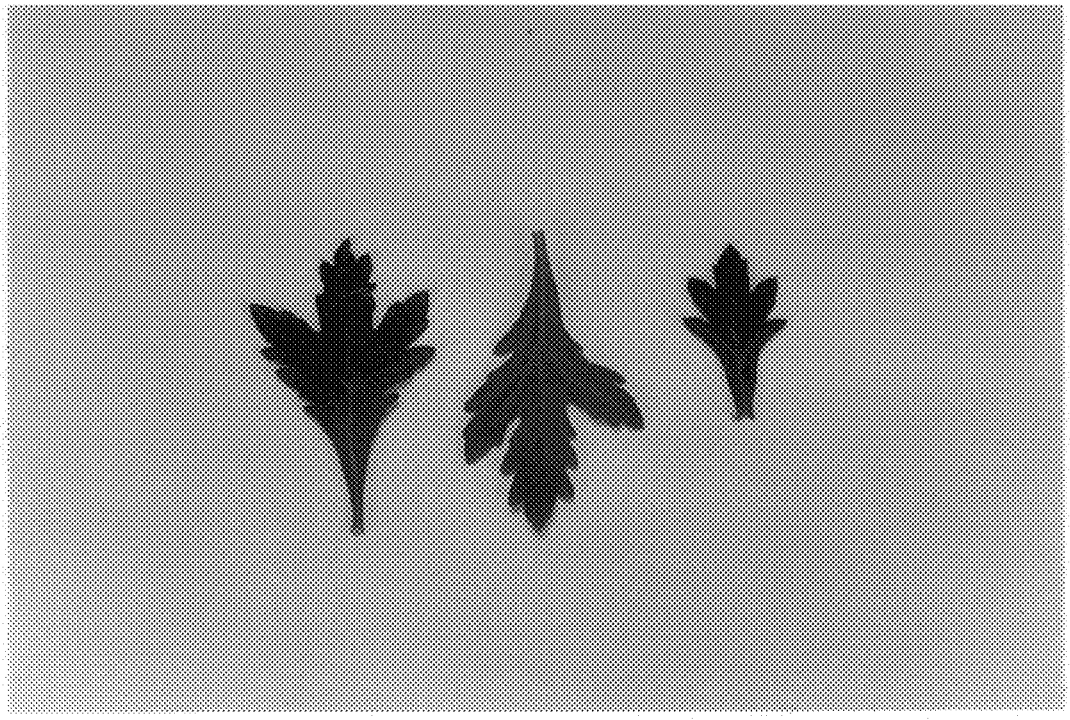
FIG. 3 shows the various stages of foliage and petiole of the new cultivar.

This new variety of chrysanthemum is of the botanical classification *dendranthema grandiflora*. The observations and measurements were gathered from plants grown in a greenhouse in Rijsenhout Holland in a photo-periodic controlled crop under conditions generally used in commercial practice. The greenhouse temperatures during this crop were at day-time between 18° C. and 25° C. and at night 20° C. The photo-periodic response time in this crop was 47 days after an average of eight long days. After this long day period to flowering growth retardants were applied 6 times in an average dose of 1.5 gram/liter water. No tests were done on disease or insect resistance or susceptibility. This new variety produces small sized blooms with pale pink ray-florets and yellow-green disc-florets blooming on the plant for 5 weeks. This new variety of chrysanthemum has been found to retain its distinctive characteristics throughout successive propagations however the phenotype may vary significantly with variations in environment such as light intensity and temperature. To show the phenotype as described 'VALENTIN' can be planted without assimilation lightning (high pressure sodium lamps) between week 50 and week 40 of the next year under greenhouse conditions in Holland. With assimilation lightning (minimum level 2500 lux) it can be planted year round under greenhouse conditions in Holland.

A distinguishing characteristic of 'VALENTIN' is the darker colored reverse side of the petals. From the varieties known to inventor only the variety HOGGAR (Ser. No. 09/561,926) is similar for this characteristic. In flower size, shape and color however, HOGGAR is very different form 'VALENTIN'. A comparison is made in table 2.

The following is a description of the plant and characteristics that distinguish 'VALENTIN' as a new and distinct variety. The color designations are taken from the plant itself. Accordingly, any discrepancies between the color designations and the colors depicted in the photographs are due to photographic tolerances. The color chart used in this description is: The Royal Horticultural Society color chart, edition 1995.

TABLE 1

Botanical Description of CULTIVAR 'VALENTIN'

| | |
|---|---|
| Bud | |
| Size | Small; cross-section 0.9 cm, height 0.7 cm |
| Outside Color | Red-purple 74 B |
| Involucral bracts | 2 rows, length 7 mm, width 3 mm |
| Involucral bracts | Not present |

TABLE 1-continued

| Botanical Description of CULTIVAR 'VALENTIN' | |
|---|---|
| among disc-florets | |
| Involucral bracts color | Green 138 A |
| Bloom | |
| Type | Daisy |
| Height | Flat |
| Size | Small |
| Fully Expanded | 4.0–4.5 cm. |
| Number of blooms per branch | Approx. 5–6 blooms per branch |
| Performance on the plant | 5 weeks |
| Seeds | Not produced |
| Fragrance | Typical chrysanthemum |
| Color | |
| Center of the flower (disc-florets) | Immature yellow-green 151 A<br>Mature yellow-green 151 D |
| Color of upper surface of the ray-florets | Red-purple 69 B |
| Color of the lower surface of the ray-florets | Red-purple 74 D |
| Tonality from Distance | A pot mum with pale pink flowers and a purple buds |
| Discoloration to color | Red-purple 69 C |
| Ray florets | |
| Texture | Upper and under side smooth |
| Number | 30–32 (2 rows) |
| Cross-section | Flat |
| Longitudinal axis of majority | Straight |
| Length of corolla tube | Very short |
| Ray-floret length | 2.0–2.2 cm. |
| Ray-floret width | 0.7–0.9 cm. |
| Ratio length/width | Low |
| Shape of tip | Round |
| Disc florets | |
| Disc diameter | 1.0–1.2 cm. |
| Distribution of disc florets | Numerous clearly visible at all stages of flowering. |
| Shape | Tubular |
| Color | Yellow-green 151 A |
| Receptacle shape | Conical raised |
| Reproductive Organs | |
| Stamen (present in disc florets only) | Yellow, thin, 3 mm. in length |
| Number of stamen | Grown together as one |

TABLE 1-continued

| Botanical Description of CULTIVAR 'VALENTIN' | |
|---|---|
| Stamen color | Yellow-green 144 C |
| Pollen | Present |
| Pollen color | Yellow-orange 13 A |
| Styles (present in both ray and disc florets) | Yellow-green, thick |
| Style color | Yellow-green 144 C |
| Style Length | 3 mm. |
| Stigmas | Green-yellow |
| Stigma Width | 1 mm. |
| Ovaries | Enclosed in calyx |
| Plant | |
| Form | A pot mum meant for indoor use |
| Growth habit | Spreading |
| Growth rate | Moderate |
| Height | 19.0–21.0 cm. |
| Width | 22.0–24.0 cm. |
| Stem Color | Green 138 A |
| Stem Strength | Weak |
| Stem Brittleness | Absent |
| Stem Anthocyanin Coloration | Absent |
| Length of lateral branch | From top to bottom 11–12 cm. |
| Lateral branch color | Green 138 A |
| Lateral branch, attachment | Weak |
| Branching (average number of lateral branches) | Pralific with 4–5 breaks after pinching |
| Peduncle length | 2.0–2.5 cm. |
| Peduncle color | Green 138 A |

TABLE 2

| Differences with the comparison varieties | |
|---|---|
| 'VALENTIN' | 'HOGGAR' |
| Color of upper surface of ray florets Red-purple 69 B | Yellow 12 A |

I claim:

1. A new and distinct variety of chrysanthemum plant as described and illustrated.

* * * * *